United States Patent [19]

Rembaum

[11] 4,046,750
[45] Sept. 6, 1977

[54] IONENE MODIFIED SMALL POLYMERIC BEADS

[75] Inventor: Alan Rembaum, Altadena, Calif.

[73] Assignee: California Institute of Technology, Pasadena, Calif.

[21] Appl. No.: 510,786

[22] Filed: Sept. 30, 1974

[51] Int. Cl.² ................................................ C08F 8/30
[52] U.S. Cl. ................................ 526/310; 204/159.22; 210/37 R; 424/2; 424/25; 424/78; 424/271; 424/329; 260/33.2 R; 260/42.21; 260/80.3 N; 260/86.1 R; 260/86.1 N; 260/86.1 E; 526/292; 526/296; 526/328
[58] Field of Search .......... 260/80.73, 80.3 N, 86.1 R, 260/86.1 N, 86.1 E

[56] References Cited

U.S. PATENT DOCUMENTS

| | | | |
|---|---|---|---|
| 3,043,822 | 7/1962 | Maeder | 260/89.7 |
| 3,054,782 | 9/1962 | Saxon | 260/80.5 |
| 3,644,225 | 2/1972 | Quentin et al. | 260/2.1 E |
| 3,689,470 | 9/1972 | Shachat et al. | 260/86.1 N |
| 3,808,158 | 4/1974 | Bolio | 260/2.1 R |
| 3,857,824 | 12/1974 | Atkins | 260/80.3 N |

*Primary Examiner*—John Kight, III
*Attorney, Agent, or Firm*—Marvin E. Jacobs

[57] ABSTRACT

Linear ionene polyquaternary cationic polymeric segments are bonded by means of the Menshutkin reaction (quaternization) to biocompatible, extremely small, porous particles containing halide or tertiary amine sites which are centers for attachment of the segments. The modified beads in the form of emulsions or suspensions offer a large, positively-charged surface area capable of irreversibly binding polyanions such as heparin, DNA, RNA or bile acids to remove them from solution or of reversibly binding monoanions such as penicillin, pesticides, sex attractants and the like for slow release from the suspension.

8 Claims, 2 Drawing Figures

IONENE MODIFIED SMALL POLYMERIC BEADS

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

BACKGROUND OF THE INVENTION

1. Field of the Invention

The present invention relates to small, polymeric beads and, more particularly, to linear ionene modified beads for use in binding small and large anionic compounds.

2. Description of the Prior Art

It is believed that certain clinical hemorrhagic states are associated with a heparin-like substance in the blood. In addition, the value of antiheparin agents lies also in the treatment of post-partum hemorrhage and the restoration of normal blood coagubility after open heart surgery and after hemodialysis, where administration of relatively large doses of heparin is a common practice. Protamine sulfate and toluidine blue, neither of which are free of toxic effects, are clinically used as antiheparin agents.

Polycations obtained by the Menshutkin reaction of aliphatic diamines with aliphatic dihalides or by homopolymerization or dimethylamino-n-alkyl halides are referred to as ionenes. The ionenes constitute a unique system because of their structure, their distances between positive charges, their counterions and their molecular weight can be varied systematically. They form strong, insoluble complexes with heparin, the concentration of which can be determined by a simple potentiometric titration.

Studies have shown that the heparin concentration in water in low ionic strength can be determined by following the pH changes of a heparin solution when ionenes are gradually added to it. Quantitative yields of heparin ionene complexes are obtained at the neutralization point. The amount of ionene necessary to neutralize a given amount of heparin depends on the charge density of the ionene and can be determined by means of this pH titration. In addition, this procedure also offers information of the stoichiometry of polycation polyanion complexes and on the charge density of polyelectrolytes in general.

Although most ionene structures have antiheparin activity, extensive investigations of toxicology and effects on the circulatory system in laboratory animals were carried out only with 6,3-ionene bromide referred to as "Polybrene." The latter was found to be more toxic (i.v. $LD_{50}$, 28 mg/kg in mice and 20 mg/kg in rats; the i.p. $LD_{50}$ in mice is 61.5 mg/kg) than toluidine blue (i.v. $LD_{50}$, 45 mg/kg) and protamine sulfate (i.v. $LD_{50}$, 44 mg/kg). However, cumulative i.v. doses of 6,3-ionene bromode up to 5 mg/kg as 1 percent solutions could be given rapidly to anesthetize dogs without markedly affecting either the respiration or circulation, i.e., without toxic symptoms.

Heparin offers a protective action in neutralizing the toxicity of 6,3-ionene bromide in both mice and dogs. Thus pre-treatment of mice with heparin enabled them to survive doses of three times the $LD_{50}$ values with only mild toxicity symptoms.

SUMMARY OF THE INVENTION

It has now been discovered in accordance with the invention that ionenes covalently bound to small, polymeric spheres can be utilized for the efficient removal of heparin from aqueous solution or for general use in binding anions and polyanions of diverse nature in separation, analytical, diagnostic and clinical applications. The cationic modified beads provide a large surface area and form water-insoluble complexes with anions, removing them from solution.

The uniformly-shaped, porous beads are formed by the aqueous suspension copolymerization of a halo- or dimethylaminosubstituted acrylic monomer and a cross-linking agent. Cross-linking proceeds at high temperature above about 50° C or at lower temperture with irradiation. Beads of even shape and size of less than 2 micron diameter are formed in the presence of an aqueous soluble polymer such as a polyether and of a larger size in the absence of a polyether or in the presence of a soluble monomer such as 2-aminoethylmethacrylate or allyl amine. The beads are separated and reacted with a mixture of a ditertiary amine and a dihalide or with a dimethylaminoalkyl halide to attach ionene segments to the halo or tertiary amine centers on the beads. The insoluble cationic modified beads are readily separated from soluble ionene homopolymer that is formed.

Large sized beads of the order of 50 micron diameter will find use in affinity or pellicular chromatography. The column of beads preferentially removes heparin from its mixture with polycations or neutral substances such as proteins or serums. The cationic beads can be used in the separation of cholesterol precursors such as bile acid from bile micellar suspensions.

The beads bind RNA or DNA irreversibly and smaller size beads have been found to penetrate the membrane of living cells and enter the nucleus thereof. The cationic modified beadsalso show cytoxic activity toward malignant cells.

The beads form weak reversible complexes with anionic compounds containing 1–5 anionic groups, permitting slow release of the anionic compound from suspension. Thus, suspensions will find use in the substained release of nutrients, hormones, vitamins, pharmaceuticals, sex attractants, pesticides in clinical agriculture and maricultural applications. Penicillin is found to be slowly released from a suspension of ionene treated beads. The binding of cytoxic drugs such as Methotrexate to the beads should provide increased activity due to the cytoxic activity of the ionene.

The cationically charged spheres can also be used as markers of negative sites on living cells or tissue and the charged spheres undergo phagocytotic action by these cells. The presence of OH, COOH and amine groups on the beads permits covalent binding of biomolecules such as haptens, enzymes, antibodies or lectins to the beads by means of cyanogen bromide, carbodiimide or glutaraldehyde reactions.

The labeled beads can be utilized for the diagnosis of conditions such as hepatitis, gonorrhea, rheumatoid arthritis, streptococcus infections and pregnancy by mixing the labeled beads with a body serum and observing whether the beads bind to specific antigen sites causing precipitation or agglutination. The labeled beads may also be utilized in the treatment of the diseased condition by the use of the bound specific biomolecular agent to direct the bead to the desired cell and the toxic action of the polyquaternary function on the cell.

The toxicity of the ionene function is considerably decreased if not eliminated by complexation with the above-mentioned polyanions. The complex is taken up by living cells easier than the separate components since in the bead complex all charges are neutralized. This activity is of particular interest since it has previously been discovered that ionene-RNA complexes have antiviral activity.

These and many other attendant advantages will become apparent as the invention becomes better understood by reference to the following detailed description when considered in conjunction with the accompanying drawings.

DESCRIPTION OF THE PREFERRED EMBODIMENTS

Figure 1:
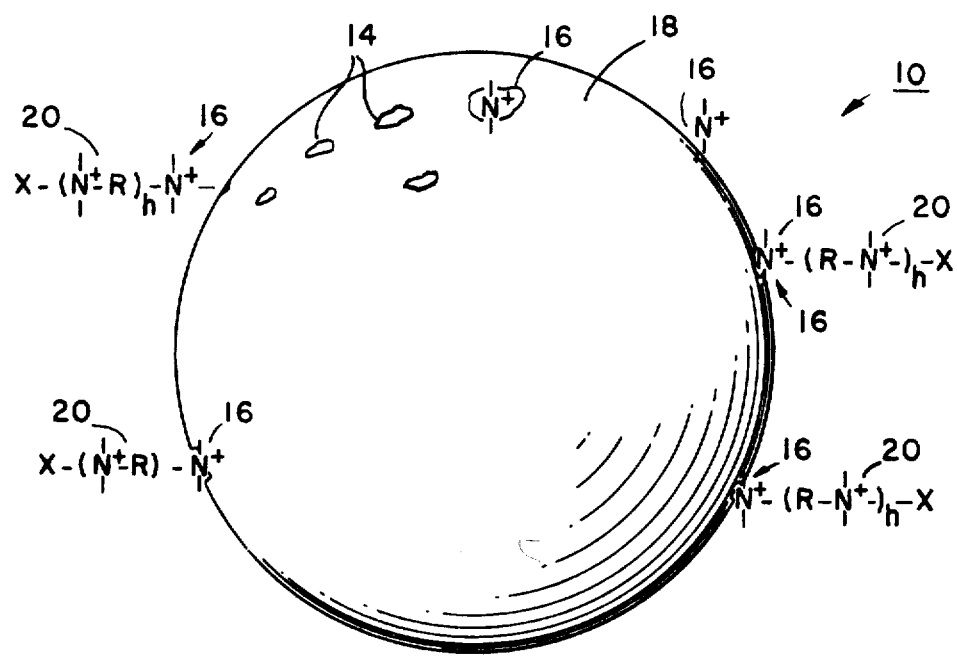
FIG. 1 is a schematic view of an ionene-modified bead according to the invention.

The bead 10 as shown in FIG. 1 is a small, essentially spherical particle having pores 14 and containing ionene reactive halide or tertiary amine groups 16 throughout the bead 10 and on the surface 18. Ionene segments 20 extend from the surface of the bead.

The beads are prepared by the aqueous suspension polymerization of a monounsaturated, bromo, chloro, iodo or tertiary amine substituted acrylic monomer and 0.1 to 30% by weight of a cross-linking agent. Polymerization proceeds at a temperature above 50° C, preferably 70° C, to reflux in the presence or absence of a free radical catalyst or at a lower temperature of −70° C to 70° C with application of high energy radiation to the polymerizable mixture. Smaller beads of uniform spherical shape of the order of 0.1 to 2 microns or smaller are favored in the presence of 0.1 to 5% by weight of a water soluble polymeric suspending agent such as polyether having a molecular weight from 300,000 to 6,000,000 such as polymers of ethylene oxide, propylene oxide or mixtures thereof.

The ionene reactive monomer is suitably a compound of the formula:

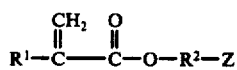

where R¹ is hydrogen or lower alkyl of 1-8 carbon atoms, R² is alkylene of 1-12 carbon atoms and Z is chloro, bromo, iodo or

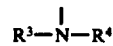

where R³ and R⁴ are alkyl of 1-3 carbon atoms. Suitable compounds are dimethylaminoethylmethacrylate and 2-bromoethylmethacrylate.

The ionene reactive monomer may be mixed with up to 97% by weight of a compatible comonomer such as a lower alkyl methacrylate, acrylic acid, methacrylic acid, styrene, vinyl toluene, acrylamide or hydroxyl alkyl or amino alkyl substituted acrylates of the formula:

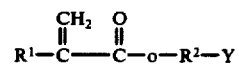

where R¹ and R² are as defined above and Y is OH or

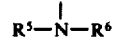

where R⁵ is hydrogen and R⁶ is hydrogen, lower alkyl or lower alkoxy of 1-8 carbons atoms. Representative compounds are hydroxyethyl-methacrylate, hydroxypropylmethacrylate, 2aminoethyl methacrylate.

The cross-linking agent is present in the polymerizable mixture in an amount from 0.1 to 30%, preferably 1-6% by weight, and is a polyunsaturated compound such as a diene or a triene capable of addition polymerization with the unsaturated group of the monomer. Suitable compounds are low molecular weight polyvinyl compounds such as ethylene glycol dimethyacrylate, divinyl benzene, trimethylol propane trimethacrylate and N,N′-methylene-bis-acrylamide (BAM).

A commercial form (94%) of hydroxyethylmethacrylate (HEMA) and hydroxypropyl methacrylate (HPMA) as supplied, contains small amount of methacrylic acid, hydroxyalkoxyalkylmethacrylate and dimethacrylates - ethylene glycol dimethacrylate in HEMA and propylene glycol dimethacrylate in HPMA. HPMA is generally a mixture in which the principal monomers comprise 68-75% of 2-hydroxypropyl and 25-32% of 1-methyl-2- hydroxyethylmethacrylate. Typical compositions in weight percentage follows:

| Compound | HEMA 94% | HPMA 94% |
|---|---|---|
| Hydroxyalkylmethacrylate | 86 | 87 |
| Higher boiling methacrylate, principally hydroxyalkoxy-alkylmethacrylate | 6 | 5 |
| Methacrylic Acid | 3.5 | 4.5 |
| Dimethacrylate | 1.5 | 0.7 |

The monomers are diluted in aqueous medium at a level of from 0.5 to 50% by weight, preferably 1-20% by weight. The aqueous medium comprises water and the soluble polymer. Water soluble polymeric stability agents such as polyvinyl, pyrrolidone or polyether may be present in an amount as low as 0.05 weight percent. Amounts above 5% are believed unnecessary and require added time and effort to remove the polymer from the final beads.

Finely and uniformly shaped and sized beads have consistently been produced in an aqueous medium containing a stabilizing agent such as a polyether. The polyethers generally have a molecular weight from 300,000 to 5,000,000, preferably 400,000 to 2,000,000, and are polymers of alkylene oxides such as ethylene oxide, propylene oxide or their mixtures. Polyethylene oxides are preferred due to their solubility in water.

The polymerization proceeds with or without catalyst and with or without stirring with application of heat to the mixture at a temperature of from 70° C to reflux, generally about 100° C or with application of high energy radiation capable of generating free radicals and initiating polymerization and forming cross-linking bonds between olefinic groups. Surprisingly mono-dispersed beads of fairly even size range are formed without the presence of an emulsifying agent. The presence of the dimethylamino monomer stabilized the beads in that they do not coalesce in suspension as compared to beads containing carboxyl groups. Polymerization proceeds by application of 0.05 to 1.0 megarads of radiation from a cobalt gamma source at a temperature of 0° C to 70° C. The reaction is preferably conducted under oxygen excluding conditions, generally by applying vacuum to the reaction vessel or by bubbling inert gas such as nitrogen through the mixture. A free radical catalyst such as ammonium persulfate and additional agents such as other suspending or emulsifying agents such as sodium lauryl sulfate may be present in the polymerizable mixture.

After polymerization has proceeded to completion, the polymerization mixture is diluted with hot water and filtered and washed with boiling water to remove the polyether or simply centrifuged without dilution. The dry material in over 90% yield is in the form of separate round beads or agglomerates of beads. Agglomerates, if present, are subdivided into beads mechanically by dispersion in a non-solvent liquid, crushing or grinding. The beads are uniformly sized and at least 80 percent, and preferably at least 90 percent, of the beads are of a uniform diameter less than 5 microns, preferably from 500A. to 2 microns. The cross-linked porous beads are insoluble and swellable in water and are insoluble in common inorganic and organic solvents.

Specific examples of practice follow.

EXAMPLE 1

The following aqueous mixture was prepared.

| Component | Weight, gm |
|---|---|
| HEMA (Freshly distilled containing 1.5% ethylene dimethacrylate) | 40 |
| Trimethylol propane trimethacrylate (TPT) | 6.0 |
| Polyethylene oxide (M.W. $10^6$) | 4.0 |
| Dimethylaminoethyl methacrylate | 10 |
| Water to one liter | |

The mixture was nitrogen inerted and 0.1 megarads of radiation was applied to the mixture at room temperature from a cobalt gamma source. The beads were filtered, washed with boiling water several times and centrifuged to provide a 99 percent yield. Under scanning electron microscope, the diameter of over 90 percent of the beads was determined to be from 1–2 microns. The copolymer beads contain hydroxyl as well as dimethylamino groups. The procedure was repeated at 0° C in ice bath with 0.2 and 0.4 megarads with similar results.

EXAMPLE 2

The following aqueous mixture was prepared.

| Component | Weight, gm |
|---|---|
| HEMA | 60 |
| Dimethylaminoethyl methacrylate | 10 |
| TPT | 2.0 |
| Polyethylene oxide (M.W. $10^6$) | 4.0 |
| Water to one liter | |

The mixture was nitrogen inerted and subjected to 0.4 megarads of cobalt gamma radiation. Individual beads of about 1 micron diameter were produced.

EXAMPLE 3

The following aqueous mixture was prepared.

| Component | Weight, gm |
|---|---|
| HEMA | 35 |
| Dimethylaminoethyl methacrylate | 15 |
| N,N'methylene bis acrylamide | 6.0 |
| Polyethylene oxide (M.W. 10hu 6) | 4.0 |
| Water to one liter | |

The mixture was polymerized under the condition of Example 2 to yield individual beads having a well characterized diameter of about 0.9 microns.

The tertiary amine or halogen modified beads are then reacted with linear ionene forming reactants such as (1) α,ω-dihalo alkane or (2) with dimethylamino-η-alkyl chloride. The two reactions for a 3-Ionene Bromide can be represented as follows:

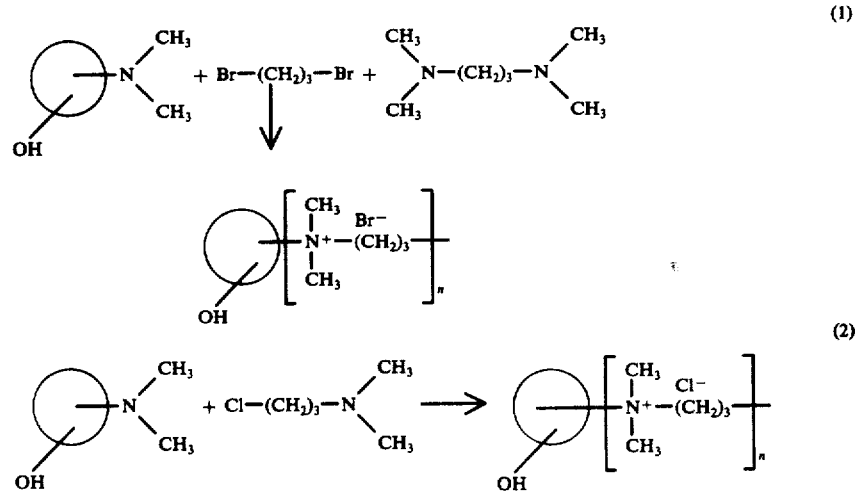

Both reactions yielded aqueous suspensions of spheres (with 3-ionene on the surface) observable under an ordinary light microscope. The presence of ionenes can be demonstrated qualitatively by the use of anionic dyes; Trypan blue and Eosin Y are removed from aqueous solutions by means of ionene spheres.

The ionene polymers of interest in this interest in this invention are water-soluble, linear polymers, without cross-linking or branching. The polymer segments have a molecular weight from 500 to 100,000, generally from 1,500 to 60,000, and have an average charge of at least one intra polymeric quaternary nitrogen for an average of every twelve chain atoms.

The ionene modified beads have the general structure:

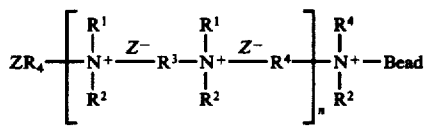

where $R^1$ and $R^2$ are methyl, $R^3$ and $R^4$ are divalent aliphatic, aromatic or heterocyclic groups containing at least 3 carbon atoms, or $R^3$ combined with $R^1$ and $R^2$ forms a cyclic group and $Z^-$ is an anion, generally chloro, bromo or iodo.

Aliphatic ionene polymers in which $R^3$ and $R^4$ are the same polymethylene group of the formula $(CH_2)_x$ where $x$ is 3 or more than 6 can be prepared by homopolymerization of tertiary amino alkyl halides of the formula $$Z(CH_2)_x N(CH_3)_2$$

in accordance with the procedure disclosed in copending application Ser. No. 280,649, filed Aug. 14, 1972. Values of $x$ between 4 and 7 result in cyclic products. Generally the polymerization is conducted in water at a concentration of monomer above 3 molar, at a temperature from 80–110° C under oxygen excluding conditions.

Ionenes can also be prepared by the copolymerization of ditertiary amines and dihalo organic compounds. This reaction permits the synthesis of a variety of linear polymers in which the distance between positive nitrogen centers can be varied at will. With aliphatic ionenes of the formula:

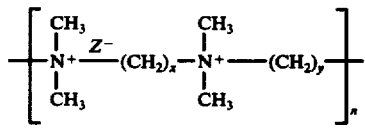

the values of $x$ and $y$ between 3 and 16 must also be selected to avoid formation of cyclic compounds, as disclosed by Rembaum et al., *Macromolecules* 5 261 (1972), the disclosure of which is incorporated herein by reference.

Well defined conditions of synthesis relating to formation of relatively high molecular weight ionenes are disclosed by Rembaum et al., *J. Polym. Sci.*, Part B 6 (1968), the disclosure of which is incorporated herein by reference. Generally, high molecular weight ionene polymers are prepared in a 0.1 to 2.5 molar solution of a ditertiary amine and a dihalo organic compoundin solvent at temperatures below about 50° C. Higher polymerization rates occur in polar organic solvents such as dimethyl formamide (DMF), dimethyl sulfoxide (DMSO), methanol, preferably a mixture of DMF and methanol.

The dihalo organic material is a compound of the formula $ZR^4Z$ where Z is chloro, bromo or iodo, where $R^4$ is a divalent organic radical such as alkylene, arylene, alkarylene or aralkylene. Hydrocarbon $R^4$ groups may also be interrupted with atoms such as nitrogen, oxygen or sulfur and may be substituted with diverse pendant groups that do not interfere with the polymerization reaction or activity of the polymer or promote undesirable side effects during use.

Representative dihalo organic compounds are α,ω-chloro or bromo terminated compounds such as 1,3-dichloropropane, 1,3-dibromopropane, 1,4-dichlorobutane, 1,4-dibromobutane, 1,4-dichloro-2-butene, 1,4-dibromo-2-butene, 1,4-dibromo-2,3-dihydroxy butane, 1,5-dichloropentane, 1,6-dibromohexane, 1,8-dichlorohexane, 1,10-dichlorodecane, and 1,16-dichlorohexadecane. The alkenylene compounds are more reactive than the corresponding saturated compounds. Dihalo aromatic compounds such as o, m, and p-dichloro or -dibromo xylene may also be utilized.

The diamine reactant for the copolymerization reaction may be represented by the formula:

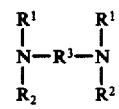

where $R^3$ is aliphatic, aromatic, heterocyclic or $R^3$ when combined with $R^1$ and $R^2$ forms a cyclic group. Representative compounds are N,N,N',N'-tetramethyl-1,3-diamino propane, N,N,N',N'-tetra-methyl-1,3-hexamethylene diamine (THD) and N,N,N',N'-tetramethyl-1,10-decamethylene diamine. Examples of heterocyclic or aromatic compounds are 1,2-bis-(4-pyridyl)-ethane, -propane or -butane, dipyridyl, diazo-bicyclooctane or tetramethyl diamino, diphenyl methane.

EXAMPLE 4

Spherical particles (1.66 microns in diameter) containing 7.64 × 10⁸ dimethylamino groups per sphere were stirred with 1,3-dibromopropane and 1,3-tetramethylamino propane at room temperature in dimethylformamide-methanol mixture (1:1 by volume) for 24 hours. The reaction product after addition of water was centrifuged. The centrifugation in presence of water was repeated until the supernatant was free of bromide ions. The spheres contained 2.9 meq of bromine per gram.

EXAMPLE 5

The spherical dimethylamino-substituted particles of Example 4 were suspended in an aqueous medium containing dimethylaminopropylchloride in 5 molar concentration. The suspension was heated at 90° C to 100° C while bubbling nitrogen through the suspension to exclude oxygen. The beads recovered as in Example 4 contained 2.1 meq of chlorine per gram of beads.

EXAMPLE 6

An aqueous suspension of the polycation spheres of Examples 4 and 5 (1 cc, 28 mg/cc; 7 × 10⁹ spheres/cc) was added to 20 ml of a heparin solution (1 mg/ml). After stirring the mixture for 15 minutes and filtration, the filtrate contained 0.04 mg of heparin per cc. By repeating this experiment under identical conditions but using 2 cc of suspended, charged shperes, no heparin could be detected in the filtrate by means of Azure A. The presence of positive charges on the spherical particles was ascertained by reaction with Eosin Y. The latter is an acidic dye which combines with 3,3-ionene to form an insoluble red precipitate. The ionene spheres were stirred in an aqueous solution with Eosin Y for 10 minutes and then centrifuged in distilled water ten times. The spheres remained dark red. Polyhydroxyethylmethacrylate spheres without dimethylamino groups served as control. After reaction with Eosin y and centrifugation, they were free of dye and appeared white.

The percentage of halide is a measure of the length of the ionene segments attached to the beads. Since the beads are porous, some ionene reaction with interior halogen or dimethylamino sites can be expected. However, the majority of the reaction is expected to proceed by linear addition to the surface sites. The amount of ionene is also dependent on the amount of amine or halogen functionality present in the bead and the size of the bead. For beads in the 0.5 to 1.5 micron range polymerized with 4–20% tertiary amino alkyl acrylate, a typical percentage for bromine is from about 1 meq to 30 meq per gram of beads.

The amount of heparin complexed with the ionene spheres in Example 6 is shown in the following table.

Table 1

| Removal of Heparin from Aqueous Solutions | | |
|---|---|---|
| | Halide meq/g | mg Heparin complexed/g of spheres |
| Ionene spheres (Ex. 4) | 2.9 | 335.7 |
| Ionene spheres (Ex. 5) | 2.1 | 300.5 |

EXAMPLE 7

Preparation of microspheres containing dimethylamino functional groups.

Freshly distilled, specially purified (about 99 percent pure) 2-hydroxyethyl methacrylate (a) containing 0.37 ethylene glycol dimethacrylate and less than 0.01 of methacrylic acid and freshly distilled 2-dimethylaminoethyl methacrylate or methacrylic acid (b) were mixed in the proportion of 4 of (a) to 1 of (b) by weight. The mixture containing 2% weight of BAM and 0.4% w/v of high molecular weight polyethylene oxide was used to make up 0.5, 3, 5 and 10% w/v solutions in distilled water.

Figure 2:
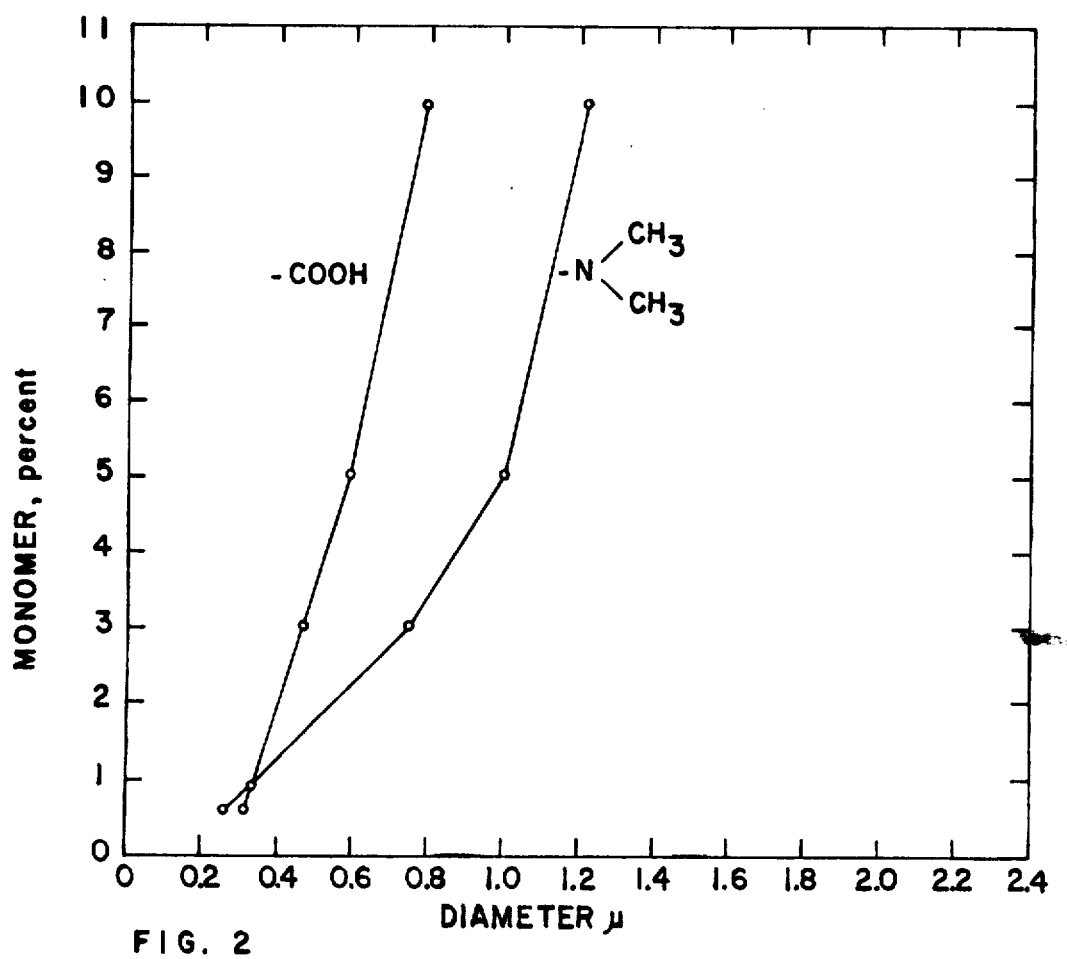
FIG. 2 is a graph illustrating the effect of acrylic acid or dimethylaminoethylmethacrylate monomer concentration on particle size.

The solutions were subjected to a Co $\alpha$ irradiation dose of 0.2 megarads. The irradiated samples were centrifuged five times at 5 to 10,000 rpm for 15 minutes. The supernatant liquor was discarded after each centrifugation and the solid was redispersed in distilled water. The diameter of the microspheres was determined by scanning electron microscopy. In FIG. 2 are shown the sizes of the microspheres as a function of total monomer concentration. The dimethylamino content varied from 1.71 to 2.2 weight % compared to a value of 1.77 weight % theoretical content.

By eliminating the PEO from the reaction mixture, the size of the microspheres could be considerably increased.

The size of the spheres obtained is somewhat larger in the bead containing dimethylamino end groups and would be of intermediate size in a copolymer containing both methacrylic acid and 2-dimethylaminoethyl methacrylate. Use of a water-insoluble monomer such as methyl methacrylate further decreases the size of the beads.

EXAMPLE 8

A water suspension containing 1g of microspheres of 1.2$\mu$ in diameter prepared in Example 7 was centrifuged and resuspended in a mixture of 50 ml dimethylformamide and methanol (4:1 v/v), 1,3-dibromopropane (2.02g) and N,N,N'N'-tetramethyl propane diamine (1.3g) were added and the mixture was stirred until the contents solidified. After leaving standing for 48 hours, distilled water was added to the mixture which was contrifuged until the supernatant did not show a precipitate or cloudiness on addition of 1 M solution of ammonium perchlorate.

EXAMPLE 9

10 ml of a 1.2 micron ionene bead suspension (20 mg/ml) prepared in Example 8 were combined with 5 ml of ox bile extract. The beads absorbed oily material and separated the bile acid and possibly some cholesterol from the aqueous micellar solution and were filtered and removed. The bile acid content of the extract was considerably reduced. Since the ionenes are bound to colldoial-sized, insoluble particles, it is believed certain that they will go through the gastrointestinal tract without passage through tissue.

EXAMPLE 10

To test the activity of ionenes on bile acids, 50 mg portions of high molecular weight, non-toxic 3,3-Ionene Bromide and 6,10-Ionene Bromide were added to 5 cc of ox bile extract. An oily layer formed in each case containing the ionene complexed to the bile acids.

EXAMPLE 11

5 mg of a sodium salt of penicillin was added to a 50 mg/100cc aqueous suspension of 1.6 micron 3-ionene modified beads. The antibacterial activity of the water increased with time demonstrating the sustained slow release of penicillin from its covalent complex with the ionene bead.

EXAMPLE 12

Normal thymocyte cells of mouse origin were incubated with a suspension of 1.6 micron beads modified with 3-ionene containing $10^5$ beads/ml and $10^8$ cells/ml. After one hour, there was no evidence of cytotoxic activity.

EXAMPLE 13

A suspension of 3-ionene beads as in Example 12 was incubated with a $10^8$ cell/ml suspension of EL-4 leukemic cells of mouse origin. After 10 minutes, Trypan blue dye was added and by visual observation it was determined that all cells in contact with the beads were dead. The results were confirmed with a 3,3-Ionene Bromide polymer.

Since the concentration of ionene on the bead is strictly controlled, the beads can be added to mixtures of normal and diseased cells without danger of cytotoxic action on the normal cells. The small, insoluble bead particles are readily dyed and observed. The small beads, especially when the ionene functionality is complexed, may be well tolerated in blood or serum living animals.

It is to be understood that only preferred embodiments of the invention have been described and that numerous substitutions, alterations and modifications may be made without departing from the spirit and scope of the invention as defined in the following claims.

What is claimed is:

1. A composition of matter comprising: small, synthetic, organic, polymeric spherical particles having a diameter from 100 A. to 100 microns which are the cross-linked, addition polymerization product of a mono-unsaturated, acrylic monomer substituted with ionene reactive chloro, bromo, iodo or tertiary amine sites with 0.1 to 30% by weight of a diene or triene capable of addition polymerization with the unsaturated group of the acrylic monomer and having covalently bonded to at least one of said sites linear, polyquaternary ionene segments having an average charge of at least one intrapolymeric quaternary nitrogen for an average of every twelve chain atoms such that the halogen content of the segments is from 1 meg to 30 meg per gram of particle to form a particle of the structure:

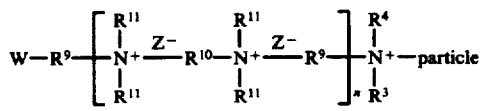

where $R^{11}$ is methyl, $R^9$ and $R^{10}$ are divalent aliphatic, aromatic or heterocyclic groups containing at least 3 carbon atoms, or $R^9$ combined with $R^{11}$ form a cyclic group, W is chloro, bromo, or iodo and $n$ is an integer.

2. A composition according to claim 1 in which the particle has a diameter form 500A. to 2 microns.

3. A composition according to claim 1 in which the acrylic monomer is present in an amount of from 2–30% by weight of the particle and is selected from compounds of the formula:

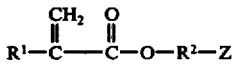

where $R^1$ is hydrogen or lower alkyl of 1–8 carbon atoms, $R^2$ is alkylene of 1–12 carbon atoms and Z is chloro, bromo, iodo or

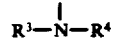

where $R^3$ and $R^4$ are alkyl of 1–3 carbon atoms.

4. A composition according to claim 3 in which the acrylic monomer is selected from dimethylaminoethylmethacrylate and 2-bromoethylmethacrylate.

5. A composition according to claim 3 in which the particle contains up to 97% by weight of at least one compatible comonomer selected from lower alkyl methacrylate, acrylic acid, methacrylic acid, styrene, vinyl toluene, acrylamide, hydroxyalkyl acrylate, or amino alkyl acrylates.

6. A composition according to claim 5 in which the comonomer is selected from compounds of the formula:

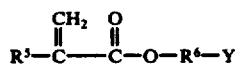

where $R^5$ is hydrogen or lower alkyl of 1–8 carbon atoms, $R^6$ is alkylene of 1–12 carbon atoms and Y is OH or

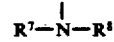

where $R^7$ is hydrogen and $R^8$ is hydrogen, lower alkyl of 1–8 carbon atoms or lower alkoxy of 1–8 carbon atoms 7. A composition according to claim 6 in which the comonomer is selected from hydroxyethylmethacrylate, hydroxypropylmethacrylate and 2-aminoethylmethacrylate.

8. A composition according to claim 1 in which $R^9$ and $R^{10}$ are alkylene from 3 to 16 carbon atoms and said segments have a molecular weight from 1,500 to 60,000.

* * * * *